United States Patent [19]

Pickl, Jr.

[11] Patent Number: 4,762,149
[45] Date of Patent: Aug. 9, 1988

[54] DOUBLE SEAL PRESS ASSEMBLED CHECK VALVE

[76] Inventor: Joseph Pickl, Jr., 860 Colliston, Ann Arbor, Mich. 48105

[21] Appl. No.: 129,343

[22] Filed: Nov. 25, 1987

Related U.S. Application Data

[63] Continuation of Ser. No. 927,650, Nov. 5, 1986, abandoned.

[51] Int. Cl.⁴ .............................................. F16K 15/14
[52] U.S. Cl. .................................... 137/843; 137/854; 285/921
[58] Field of Search ................ 137/843, 854; 251/904; 285/921

[56] References Cited

U.S. PATENT DOCUMENTS

| | | | |
|---|---|---|---|
| 2,579,855 | 12/1951 | Pockel et al. | 137/854 |
| 3,807,445 | 4/1974 | McPhee | 137/843 |
| 3,889,710 | 6/1975 | Brost | 137/843 |
| 4,147,184 | 4/1979 | Jess | 251/904 |
| 4,222,407 | 9/1980 | Ruschke et al. | 137/843 |

Primary Examiner—Robert G. Nilson
Attorney, Agent, or Firm—Harness, Dickey & Pierce

[57] ABSTRACT

A check valve consisting of two main plastic parts, namely, a valve body member and a cap member which are snapped together to form a valve chamber in which an annular valve seat is formed. A resilient disk in the valve chamber is urged to a seated position on the valve seat by a preload projection on the cap member. The two main parts are formed of a rigid or semi-rigid plastic material which is resilient enough to allow the main parts to yield enough to snap together.

6 Claims, 2 Drawing Sheets

DOUBLE SEAL PRESS ASSEMBLED CHECK VALVE

This is a continuation of U.S. patent application Ser. No. 927,650, filed Nov. 5, 1986 and entitled DOUBLE SEAL PRESS ASSEMBLED CHECK VALVE now abandoned.

This invention relates generally to check valves of the type shown in U.S. Pat. No. 3,889,710 and more particularly to a check valve of this type which is assembled by pressing two chamber forming members together and is an improvement over the check valve shown in U.S. Pat. No. 3,889,710.

BACKGROUND OF THE INVENTION

The check valve shown in the above U.S. patent consists of two members which are assembled to form a valve chamber which encloses a resilient disk and form a valve seat for the disk. One of the chamber forming members includes an inlet tube portion and the other chamber forming portion includes an outlet tube portion.

In the past, these two chamber forming members were assembled by means of sonic welding, spin welding, solvent welding, and the like and the resulting valves had the following disadvantages:

1. Some of the valves were faulty because of dimensional instability in the assembly process caused by the fact that the welding process consumes some of the plastic from which the chamber forming parts of the valve are formed. The result is non-uniformity of the valves during mass production procedures.
2. It was necessary to form both chamber forming parts of the valve of the same plastic material since assembly of the parts required welding of the parts together.
3. The sealing of the valve chamber was totally dependent on the integrity of the welding procedure.

SUMMARY OF THE INVENTION

The basic function of the press assembled check valve of this invention is to permit fluid flow in a single direction induced by a differential in the pressure from the inlet side to the outlet side of the check valve. Flow of any fluid in the opposite direction is prevented by the checking function of the check valve. The valve consists of a valve body and a valve cap which are press assembled to form a valve chamber which encloses a disk shaped elastomeric diaphragm and forms a seat for the disk. In the check valve of this invention, a preload button or projection is formed on the valve cap so that when the valve is assembled, the projection will enage the diaphragm disk and hold it in position against the seat so that it will perform its intended function.

In any such valve, the axial dimensional relationship between the valve seat, the elastomeric disk, and the preload projection are critical to the desired function of the check valves. This dimensional relationship generally requires close tolerances in the manufacture and assembly of the components. Also critical to the performance of any check valve is the integrity of the seal between the valve body and the valve cap which form the valve chamber in which the disk diaphragm is enclosed. In the check valve of this invention, the valve body and the valve cap coact so that in final assembly tubular portions of these components are relatively telescoped and provided with a pair of engaged sealing surfaces to insure airtight sealing of the valve chamber. Also, the dimensional relationship between the components is always the same to insure uniformity of the valves and reliability of operation of the valves to perform their checking functions.

The press assembled check valve of this invention is thus an improvement over the valve shown in U.S. Pat. No. 3,889,710 from the standpoints of reliability, uniformity, versatility and ease of assembly.

Further objects, features and advantages of the invention will become apparent from a consideration of the following description when taken in connection with the appended claims and the accompanying drawing in which:

Figure 3:
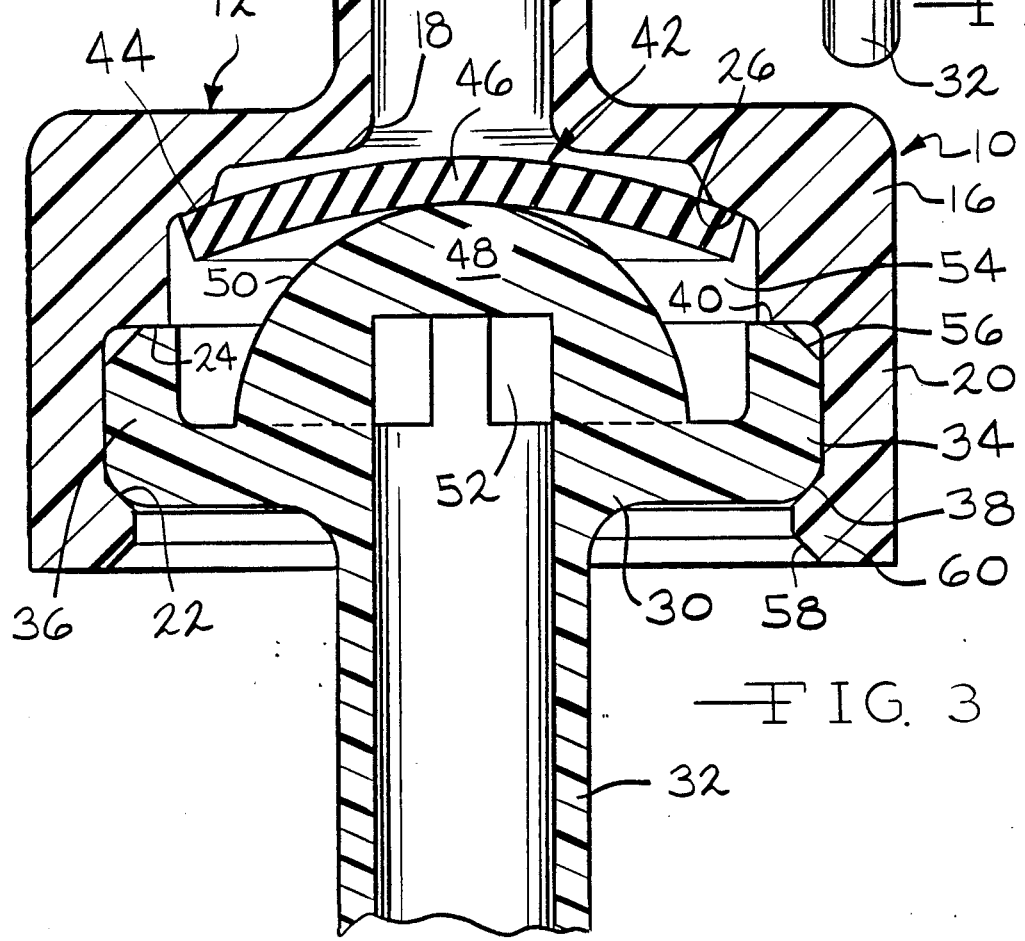
FIG. 3 is a longitudinal sectional view of the check valve of this invention as viewed from substantially the plane represented by the line 3—3 in FIG. 1.

With reference to the drawing, the check valve of this invention, indicated generally at 10, is illustrated in FIG. 3 as including a valve body member 12 having an inlet tube portion 14 and a chamber forming portion 16 at one end of the inlet portion 14. The chamber forming portion 16 is annular in shape and in diameter larger than and generally concentric with the inlet tube portion 14. The chamber forming portion 16 also has an axial inlet 18 from the inlet tube portion 14. The chamber forming portion 16 also terminates in a generally tubular section 20 having axially spaced sealing surfaces 22 and 24. The chamber forming portion 16 also has an inner shoulder 26 which forms an annular seat 26 concentric with the inlet 18 and which, as will more clearly appear hereinafter, functions as a valve seat.

The check valve 10 can also include a cap member 30 which has an oulet tube portion 32 that is integrally formed with a larger diameter chamber forming portion 34 at one end of the tube portion 32. The chamber forming portion 34 terminates in a generally tubular section 36 which is concentric with the outlet tube portion 32 and has a pair of sealing surfaces 38 and 40 formed at its ends.

The check valve 10 also includes a resilient disk or diaphragm member 42 which is formed of an elastomeric material such as rubber or a similar plastic material and is of a diameter corresponding substantially to the diameter of the valve seat 26. As a result, the disk 42 is movable to a position in which a radially outer portion 44 of the disk 42 is seated on the valve seat 26. A center portion 46 of the elastomeric disk 42 is engaged by a preload button or projection 48 that is formed on the cap member 30. As shown in FIG. 3, the preload projection 48 deflects the valve member 42 so that it is of a somewhat concave shape and is seated on the valve seat 26.

Figure 1:
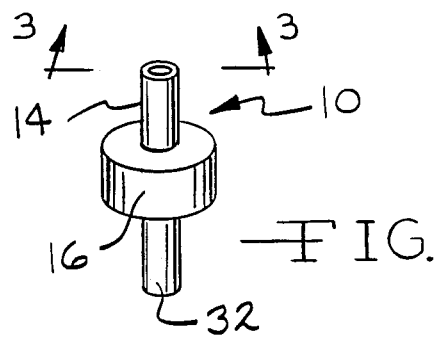
FIG. 1 is a perspective view of the press assembled check valve of this invention.
Figure 2:
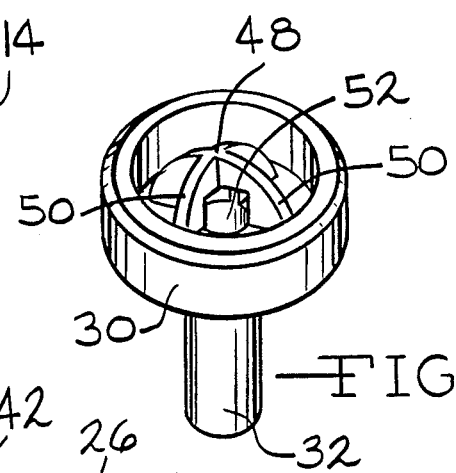
FIG. 2 is a perspective view of the valve cap in the check valve of this invention.

As shown in FIG. 2, the preload projection 48 consists of two or more arched members 50 which are arranged criss-cross fashion in a generally co-axially relation with the outlet portion 32 and are shaped so that they form an opening 52 which communicates the valve chamber 54 with the outlet tube portion 32.

In the assembly of the check valve 10, the tubular section 34 of the cap member 30 is telescoped into the tubular section 20 of the valve body member 16 to a position in which the sealing surfaces 24 and 40 are firmly engaged and the sealing surfaces 22 and 38 are similarly sealingly engaged to thereby form the generally cylindrical valve chamber 54. During telescoping of the section 34 into the section 20, an inclined outer edge surface 56 on the tubular section 34 engages a similarly inclined section 58 on a radially inwardly directed lip 60 on the tubular section 20 so as to deflect the section 20 outwardly and enable it to subsequently snap over the section 34 as shown in FIG. 3. The valve components 16 and 30 are formed of rigid or semi-rigid plastic material which has some elastic properties enabling the lip 60 to be snapped over the tubular section 34 of the cap member 30. Various well-known plastic materials such as nylon, polypropylene, acetal and the like are available for these purposes. Also, in the event that it becomes desirable in order to achieve some particular function of the valve 10, the cap member 30 and the body member 16 can be formed of different plastic materials since there is no requirement in the valve 10 of this invention that they be formed of the same material.

In the operation of the check valve 10, fluid supplied to the inlet tube portion 14 can deflect the radially outer edge portion 44 of the disk 42 in a direction away from the valve seat 26 and toward the preload projection 48 to enable fluid to flow into the chamber 54. This fluid can then flow through the passage 52 in the illustrated embodiment of the invention and into the outlet tube portion 32. Fluid flow in the opposite direction is positively checked by the disk 42.

Figure 4:
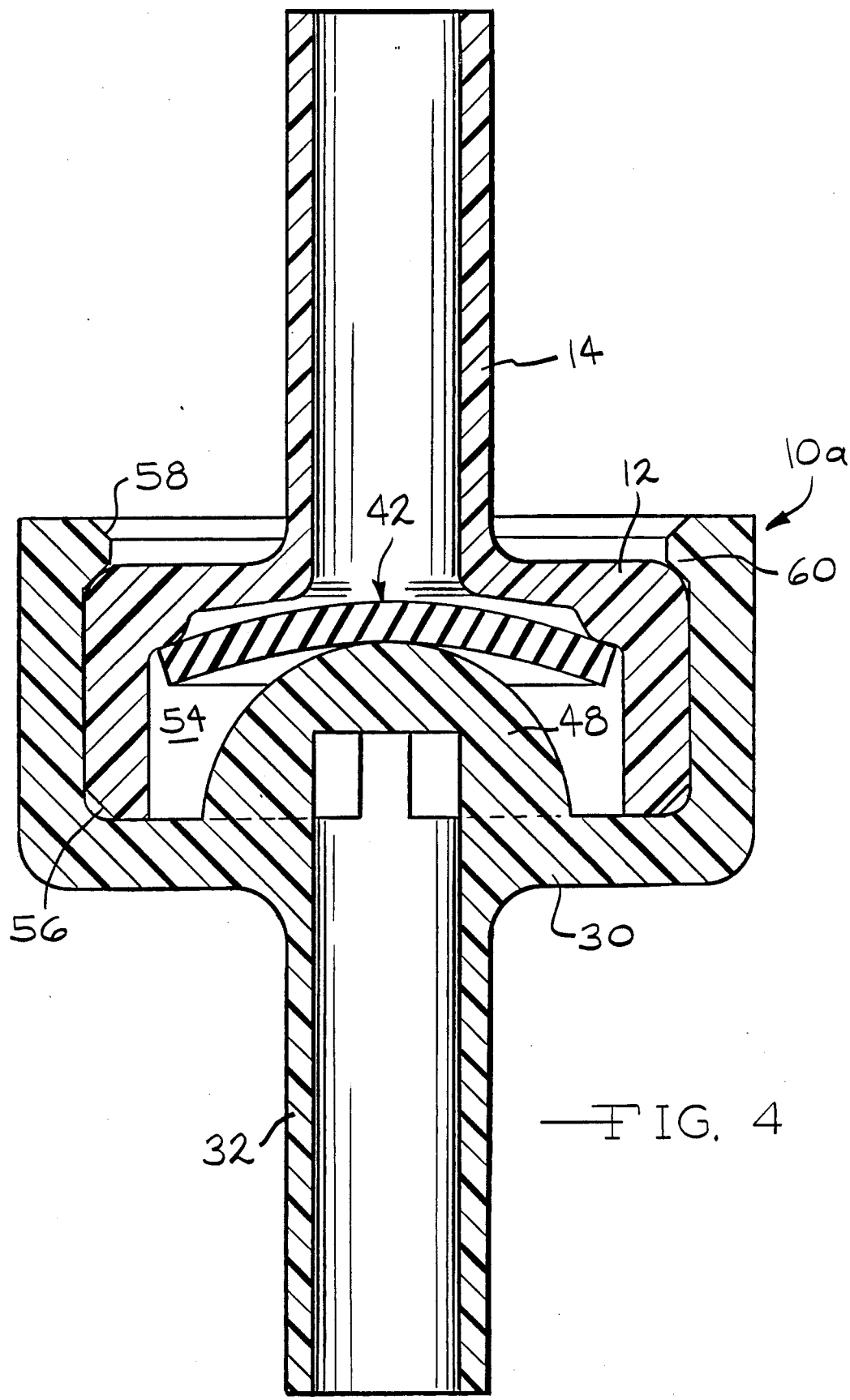
FIG. 4 is a longitudinal sectional view, like FIG. 3, of a modified form of the check valve of this invention.

FIG. 4 illustrates a modified form of the check valve of this invention, indicated generally by the numeral 10a. Valve 10a is similar in all respects to the check valve 10, and, accordingly, like numerals are used on check valve 10a to indicate like parts in the check valve 10. The check valve 10a differs from valve 10 only in that in the valve 10a the chamber forming portion 16 of the valve body member 12 is smaller in diameter than the chamber forming portion 34 of the cap member 30. Thus, in the valve 10a, the lip 60 is formed on the tubular portion 36 of the cap member 30 and it snaps over the tubular portion 20 of the body member 12. The valve 10a is assembled in the same manner as valve 10, described above, namely, by moving the members 12 and 30 axially toward each other, and operates exactly like the valve 10.

From the above description, it is seen that this invention provides improved check valves 10 and 10a which have the attributes heretofore described.

What is claimed is:

1. A check valve for use in a fluid control system comprising:

a valve body member having an inlet tube portion adapted for connection to a conduit of said system and a larger chamber forming portion at one end of and communicating with said tube portion, said chamber forming portion having an inlet from said inlet tube portion, said chamber forming portion terminating in a generally tubular section having axially spaced sealing surfaces extending around the entire periphery of said valve body, a cap member having an outlet tube portion adapted for connection to a conduit of the fluid control system and a larger chamber forming portion at one end of said tube portion, said chamber forming portion terminating in a generally tubular section communicating with said outlet tube portion and having axially spaced sealing surfaces extending around the entire periphery of said valve body, said members having said tubular sections relatively telescoped one within the other to positions in which said sealing surfaces are sealingly engaged to thereby form an enclosed valve chamber communicating with said inlet and outlet tube portions, means forming an annular valve seat in said chamber on said valve body member at a position encircling said inlet and said inlet tube portions, a resilient disk in said chamber of a size to seat on said valve seat so as to seal off said chamber from said inlet tube, and projection means on said cap member extending into said chamber and engaged with a center portion of said disk urging said disk into a position seated on said valve seat, said projection means being in a clearance relation with said disk radially outwardly of said central portion thereof to enable an annular outer edge portion of said disk radially outwardly of said central portion to move off said seat and allow passage of fluid from said inlet tube portion into said chamber, one of said tubular sections being positioned radially outwardly of the other of said tubular sections and said radially outer tubular section terminating in a radially inwardly extending lip defining one of said sealing surfaces and extending around the entire periphery of said outer tubular section and wherein said sealing surfaces of said radially outer tubular section define the axial ends of an annular cavity and the axial ends of said radially inner tubular section defining said sealing surfaces and wherein when said radially outer tubular section is snapped over said radially inner section said sealing surfaces of said radially outer tubular section exerts an axial compressive loading on said radially inner section whereby said sealing surfaces are in sealing engagement.

2. A check valve according to claim 1 further including passage means extending between said chamber and said outlet tube portion.

3. A check valve according to claim 2 wherein said projection means comprises arc shape members arranged criss-cross fashion in said chamber.

4. A check valve according to claim 1 wherein said tubular section on said valve body member constitutes said radially outer one of said tubular sections.

5. A check valve according to claim 1 wherein said tubular section on said cap member constitutes said radially outer one of said tubular sections.

6. A check valve according to claim 1 wherein said members are formed of a rigid or semi-rigid plastic material which has some elastic properties enabling said lip to be snapped over the radially inner one of said tubular sections, and means forming coacting inclined surfaces on said lip and the terminal end of said inner one of said tubular sections which are engageable and operate to flex said lip radially outwardly in response to relative axial movement of said inclined surfaces when said surfaces are in engagement.

* * * * *